(12) United States Patent
Mazlin et al.

(10) Patent No.: US 12,076,086 B2
(45) Date of Patent: Sep. 3, 2024

(54) METHODS AND SYSTEMS FOR IN VIVO FULL-FIELD INTERFERENCE MICROSCOPY IMAGING

(71) Applicants: PARIS SCIENCES ET LETTRES-QUARTIER LATIN, Paris (FR); CENTRE NATIONAL DE LA RECHERCHE SCIENTIFIQUE (CNRS), Paris (FR); ECOLE SUPERIEURE DE PHYSIQUE ET DE CHIMIE INDUSTRIELLES DE LA VILLE DE PARIS, Paris (FR)

(72) Inventors: Viacheslav Mazlin, Villebon-sur-Yvette (FR); Peng Xiao, Guangzhou (CN); Mathias Fink, Meudon (FR); Albert Claude Boccara, Paris (FR)

(73) Assignees: PARIS SCIENCES ET LETTRES—QUARTIER LATIN, Paris (FR); CENTRE NATIONAL DE LA RECHERCHE SCIENTIFIQUE (CNRS), Paris (FR); ECOLE SUPERIEURE DE PHYSIQUE ET CHIMIE INDUSTRIELLES DE LA VILLE DE PARIS, Paris (FR)

( * ) Notice: Subject to any disclaimer, the term of this patent is extended or adjusted under 35 U.S.C. 154(b) by 723 days.

(21) Appl. No.: 17/280,646

(22) PCT Filed: Sep. 27, 2019

(86) PCT No.: PCT/EP2019/076311
§ 371 (c)(1),
(2) Date: Mar. 26, 2021

(87) PCT Pub. No.: WO2020/065068
PCT Pub. Date: Apr. 2, 2020

(65) Prior Publication Data
US 2021/0345873 A1   Nov. 11, 2021

(30) Foreign Application Priority Data
Sep. 28, 2018   (EP) ...................... 18306283

(51) Int. Cl.
*A61B 3/10* (2006.01)
*A61B 3/13* (2006.01)

(52) U.S. Cl.
CPC ................ *A61B 3/102* (2013.01); *A61B 3/13* (2013.01)

(58) Field of Classification Search
CPC ...... A61B 3/102; A61B 3/13; G01B 9/02091; G01B 9/02077
(Continued)

(56) References Cited

U.S. PATENT DOCUMENTS 7,920,271 B2 * 4/2011 Vakoc .................. A61B 5/6852
356/479
2004/0085443 A1 * 5/2004 Kallioniemi ......... G06V 20/693
348/135

(Continued)

OTHER PUBLICATIONS

Viacheslav Mazlin et al : "Ultra-High Resolution Full-Field OCT for Cornea and Retina" Imaging and applied optics 2018,vo 1,1101704460 (Year: 2018).*

(Continued)

*Primary Examiner* — Mohammed A Hasan
(74) *Attorney, Agent, or Firm* — Osha Bergman Watanabe & Burton LLP

(57) ABSTRACT

According to one aspect, the invention relates to a system (101) for in vivo, full-field interference microscopy imaging of a scattering three-dimensional sample. It comprises a full-field OCT imaging system (130) for providing en face images of the sample, wherein said full-field OCT system comprises an interference device (145) with an object arm (147) intended to receive the sample and a reference arm (Continued)

(146) comprising an optical lens (134) and a first reflection surface (133), and an acquisition device (138) configured to acquire a temporal succession of two-dimensional interferometric signals ($I_1$, $I_2$) resulting from interferences produced at each point of an imaging field; an OCT imaging system (110) for providing at the same times of acquisition of said two-dimensional interferometric signals, cross-sectional images of both the sample and a first reflection surface (133) of said full-field OCT imaging system (130); a processing unit (160) configured to determine a plurality of en face images (X-Y) of a plurality of slices of the sample, each en face image being determined from at least two two-dimensional interferometric signals ($I_1$, $I_2$) having a given phase shift; determine from the cross-sectional images provided by the OCT imaging system (110) at the times of acquisition of each of said two two-dimensional interferometric signals ($I_1$, $I_2$) a depth (z) for each en face image (X-Y) of said plurality of slices; determine a 3D image of the sample from said plurality of en face images of said plurality of slices of the sample and depths.

14 Claims, 12 Drawing Sheets

(58) Field of Classification Search
USPC .......................................................... 351/208
See application file for complete search history.

(56) References Cited

U.S. PATENT DOCUMENTS

| | | | | |
|---|---|---|---|---|
| 2006/0132790 | A1* | 6/2006 | Gutin | G01B 9/02034 356/479 |
| 2016/0341539 | A1* | 11/2016 | Adie | G01B 9/02091 |
| 2017/0241765 | A1* | 8/2017 | Adie | G01B 9/02002 |
| 2019/0167109 | A1* | 6/2019 | Auksorius | A61B 5/0066 |

OTHER PUBLICATIONS

Harms, et al., Time Domain Full Field Optical Coherence Tomography Microscopy, Optical Coherence Tomography, 2015, pp. 791-812, Springer International Publishing, Switzerland.

Potsaid, et al., Ultrahigh speed 1050nm swept source/ Fourier domain OCT retinal and anterior segment imaging at 100,000 to 400,000 axial scans per second, Optics Express, Sep. 3, 2010, 20 pages, vol. 18 No. 19.

An, et al., High speed spectral domain optical coherence tomography for retinal imaging at 500,000 A-lines per second, Biomedical Optics Express, Sep. 12, 2011, 14 pages, vol. 2 No. 10.

Kraus, et al., Motion correction in optical coherence tomography volumes on a per A-scan basis using orthogonal scan patterns, Biomedical Optics Express, May 3, 2012, 18 pages, vol. 3 No. 6.

* cited by examiner

FIG. 4A
Reference mirror image
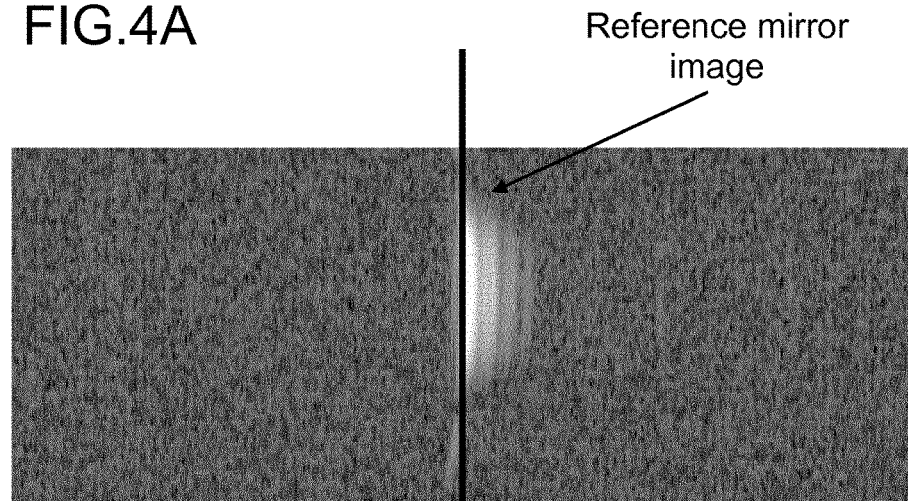
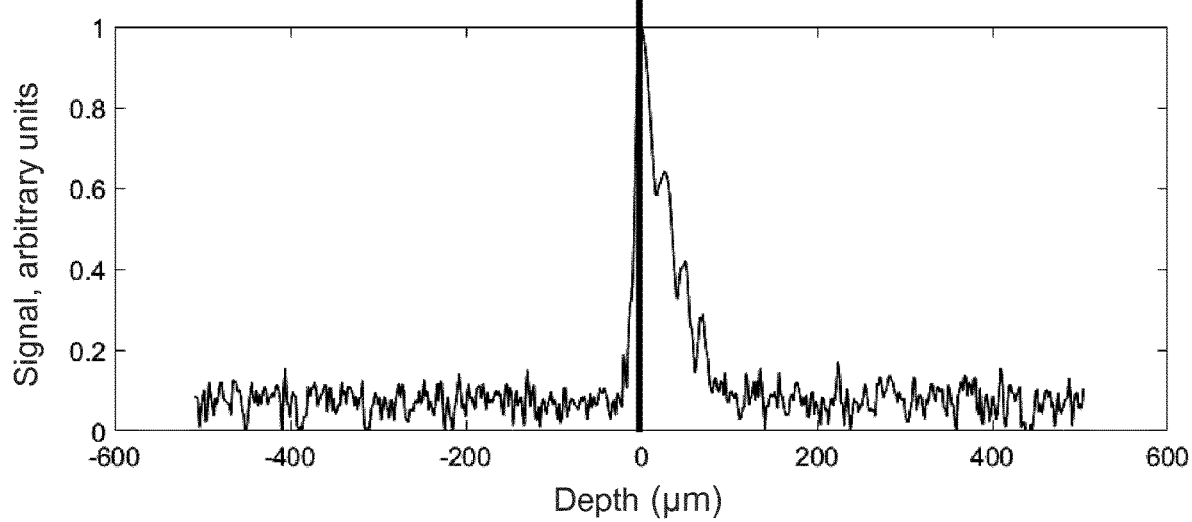
FIG. 4B

FIG.5A
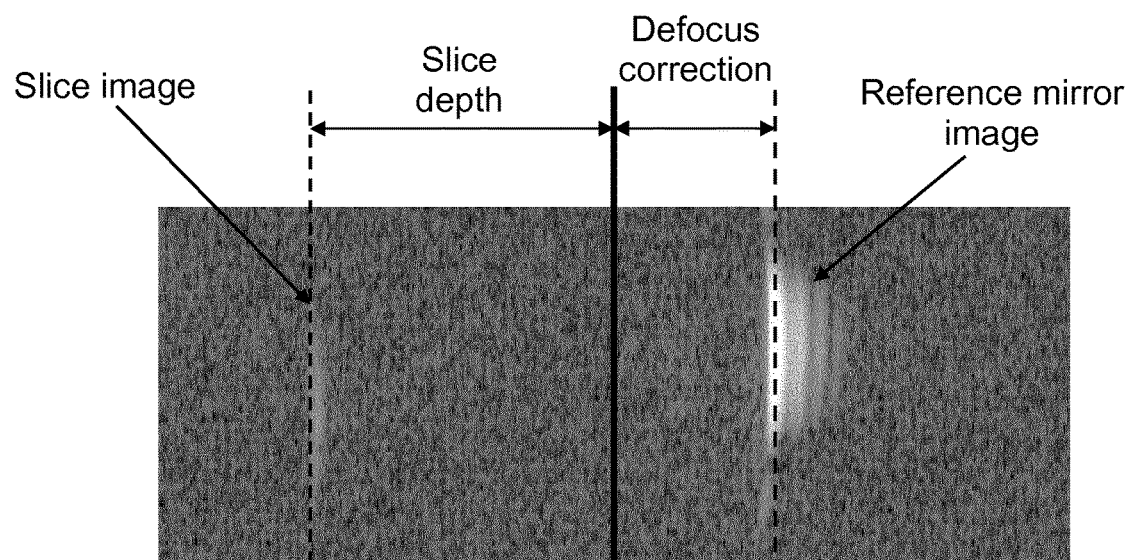
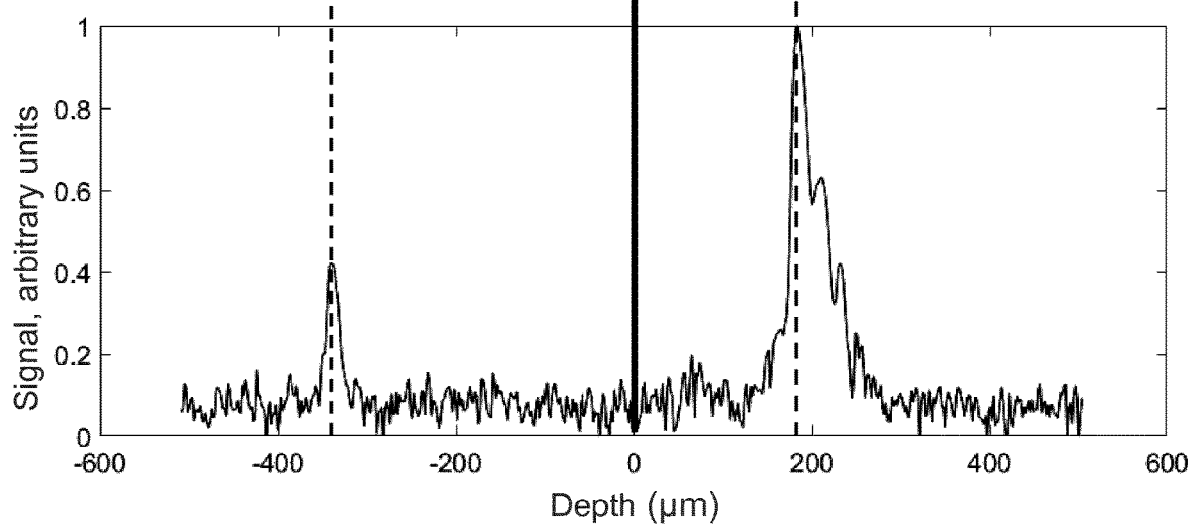
FIG.5B

METHODS AND SYSTEMS FOR IN VIVO FULL-FIELD INTERFERENCE MICROSCOPY IMAGING

TECHNICAL FIELD

The present description relates to in vivo full-field interference microscopy imaging methods and systems. It is applicable to in vivo imaging of randomly movable objects, and more particularly to in vivo imaging of ophthalmic tissues.

STATE OF THE ART

During its 25 years of development, optical coherence tomography (OCT) has become a powerful imaging modality (See for example "*Optical Coherence Tomography—Technology and Applications*"—Wolfgang Drexler—James G. Fujimoto—Editors—Springer 2015). OCT is an interferometric technique, which can be seen as an "optical analogy" of ultrasound imaging. OCT has applications in a broad spectrum of areas, and in particular in applications of the biomedical fields in ophthalmology, dermatology, cardiovascular field, gastroenterology.

In vivo tissues are involuntarily moving, and these movements have been posing challenges for all OCT techniques throughout the history. More precisely, movements lead to the appearance of misaligning, shifting and doubling artifacts in the conventional scanning OCT images. Types of the artifacts are connected with the method of OCT, according to which all the image pixels are not acquired at the same time, but rather by scanning point-by-point over the sample.

Desire to avoid these motion artifacts in the images motivated the progress in OCT technology to achieve higher imaging speeds, which resulted in spectral domain OCT (SD-OCT) (See for example L. An et al. "*High speed spectral domain optical coherence tomography for retinal imaging at 500,000 A-lines per second*"—Biomedical Optics Express 2, 2770 (2011)) and more recently swept source OCT (SS-OCT) (See for example B. Potsaid et al. "*Ultrahigh speed 1050 nm swept source/Fourier domain OCT retinal and anterior segment imaging at 100,000 to 400,000 axial scans per second*", Optics Express 18, 20029 (2010)), capable of imaging faster than 300,000 A-scans/s (1D profile). However, even at that speed of scanning, OCT images are not immune to in vivo motion artifacts.

With the same goal to get images without motion artifacts, several publications and patents suggested software and hardware-based motion compensation schemes (See for example M. Kraus et al. "*Motion correction in optical coherence tomography volumes on a per A-scan basis using orthogonal scan patterns*", Biomedical Optics Express 3, 1182 (2012)). However, hardware-based solutions are bringing additional complexity to the devices and are frequently bulky and expensive, while software based are sample- and motion-specific, meaning that they can compensate only a few types of movements only of the particular objects.

A special case of OCT, called full-field OCT (FFOCT), uses a camera to acquire all the image pixels simultaneously without point-by-point or line-by-line scanning, and is, therefore, immune to the above-mentioned artefacts. The full-field OCT imaging technique is for example described in the article "Full-field optical coherence tomography" by F. Harms et al. taken from the work "*Optical Coherence Tomography—Technology and Applications*"—pages 791-812—Wolfgang Drexler—James G. Fujimoto—Editors—Springer 2015. The full-field OCT imaging technique is also described in the French patent application FR2817030.

The full-field OCT imaging technique is based on the use of the light backscattered by a sample when it is illuminated by a light source with low coherence length, and in particular the use of the light backscattered by the microscopic cell and tissue structures in the case of a biological sample. This technique exploits the low coherence of the light source to isolate the light backscattered by a virtual slice depth wise in the sample. The use of an interferometer makes it possible to generate, by an interference phenomenon, an interference signal representative of the light originating selectively from a given slice of the sample, and to eliminate the light originating from the rest of the sample. More specifically, in order to obtain a single 2D FFOCT image, acquisition of several (typically 2 to 5) direct images on the camera is performed. Each of these direct images is acquired with a particular interference phase, which is set by a precisely positioned mirror with a piezo element (PZT) in the reference arm of the interferometer. Post-processing of these direct images with the particular phases allows to retrieve an FFOCT image.

Besides the above-mentioned immunity to the scanning artifacts, FFOCT provides higher lateral resolution by using high numerical aperture objectives than OCT since typical OCT uses relatively low NA objectives due to the requirements of large depth of field. It gives similar axial resolution by using the cheap broadband spatially incoherent illumination sources.

However, current 2D imaging scheme of FFOCT is practical for the static samples (or for in vivo samples in the moments of no or low movements), as any motion of the sample may shift the pre-determined phases and degrades the FFOCT signal or even destroys the FFOCT image. The schemes for 3D imaging are not applicable either for in vivo imaging, as locations (X, Y, Z) of the captured 2D images are becoming unknown, therefore making construction of the 3D image impossible. As a result, up to now applications of FFOCT were almost entirely limited to the static ex vivo samples.

The present description is related to devices and methods which have the advantages of full-field optical coherence tomography, and which at the same time can perform imaging of constantly moving in vivo objects.

SUMMARY

According to a first aspect, the present description relates to a method for in vivo, full-field interference microscopy imaging of a scattering three-dimensional sample comprising:
  disposing the sample in an object arm of an interference device of a full-field OCT imaging system, wherein said interference device further comprises a reference arm with an optical lens and a first reflection surface;
  producing, at each point of an imaging field, an interference between a reference wave obtained by reflection of incident light waves on an elementary surface of the first reflection surface corresponding to said point of the imaging field and an object wave obtained by backscattering of incident light waves by a voxel of a slice of the sample at a given depth, said voxel corresponding to said point of the imaging field,
  acquiring, using an acquisition device of said full-field OCT imaging system, a temporal succession of two-dimensional interferometric signals resulting from the interferences produced at each point of the imaging field;

storing, for each two-dimensional interferometric signal, a time of acquisition;

providing, at each time of acquisition of the two-dimensional interferometric signals, cross-sectional images of both the sample and said first reflection surface of said full-field OCT imaging system using an OCT imaging system;

determining a plurality of en face images of a plurality of slices of the sample, each en face image being determined from at least two two-dimensional interferometric signals having a given phase shift;

determining from the cross-sectional images provided by the OCT imaging system at the times of acquisition of each of said two two-dimensional interferometric signals a depth for each en face image of said plurality of slices;

determining a 3D image of the sample from said plurality of en face images of said plurality of slices of the sample and depths.

In the present specification, "en face images" are images determined in a plane ("X-Y" plane) perpendicular to an optical axis of the object arm (also referred to as sample arm). "En face images" are also referred as "X-Y images" or "FFOCT signal" in the present specification.

"Cross-sectional images" are images (1D or 2D) determined in a plane that contains an optical axis of the object arm. Cross-sectional images are also referred to as "X-Z images" in the present specification; however, they are not limited to a particular plane and may be determined in any plane perpendicular to the "X-Y" plane.

An "optical lens" in the present specification refers to any optical device that focuses or disperses light by means of light refraction. An "optical lens" thus encompasses both conventional optical lenses (convex, plano-convex, doublets, etc.) as other imaging systems (e.g. microscope objectives).

The imaging method thus described makes it possible to precisely determine the depth of the slice that is imaged by the FFOCT imaging system, even when imaging in vivo samples having natural movements. This is made possible by providing simultaneous acquisition of two-dimensional interferometric images using the FFOCT imaging system and the cross-sectional images provided by the OCT imaging system.

In vivo natural movements of the object can thus be used for 3D imaging, meaning that we take advantage of an effect that most of the methods try to eliminate or to overcome.

According to one or a plurality of embodiments, determining a depth for each en face image of said plurality of slices of the sample comprises determining a relative axial position of said first reflection surface and at least one identified structure of the sample in the cross-sectional images provided by the OCT imaging system.

Practically speaking, the plurality of en face images of the plurality of slices of the sample may be determined within an explored volume of the sample. Depth of an en face image of a slice is determined from OCT images from the difference between the axial location of the detected reference mirror peak and the axial location of any sample peak. It is not important, which peak of the sample is used, but typically, the brightest peak may be used. However, the same sample peak will be used throughout one volume acquisition, so that relative depths of the en face slices are correct, and a 3D image can be determined.

According to one or a plurality of embodiments, said full-field OCT imaging system and said OCT imaging system being mounted on a moving platform, the method further comprises moving said platform at least along the optical axis (Z) of the object arm to determine said plurality of en face images.

According to one or a plurality of embodiments, the method further comprises moving said platform along at least one of the directions (X, Y) perpendicular to the optical axis of the object arm. It is thus possible to stack cross-section images both axially and laterally and allow the formation of larger 3D volume (e.g. by image registration).

According to one or a plurality of embodiments, said object arm being mounted on a moving platform, the method further comprises moving said platform along an optical axis of the object arm to determine said plurality of en face images.

According to one or a plurality of embodiments, natural in vivo movements of the sample are used to determine said plurality of en face images. There is no need to move any of the platforms of said object arm or said full-field OCT imaging system and said OCT imaging system.

According to one or a plurality of embodiments, e.g. for cornea imaging, the object arm further comprises an optical lens, e.g. a microscope objective. The depth of focus of such optical lens is much smaller than the depth of focus of the eye. As a result, when the relative position of the sample arm and the sample is changed, the method further comprises moving the reference arm along an optical axis of said reference arm to compensate for defocus, i.e. keep a coherence plane within the depth of focus of the sample arm microscope objective. As a matter of fact, when moving from one medium to a second one, e.g. air and eye, a shift appears between the focus and the position that equalizes the optical paths in both arms. This defocus needs to be compensated.

According to one or a plurality of embodiments, e.g. for retina imaging, the depth of focus is high and there is no need to compensate for defocus when the relative position of the sample arm and the sample is changed.

According to one or a plurality of embodiments, the method further comprises position shifting said first reflection surface of the reference arm of the full-field OCT imaging system to provide said phase shift between said at least two two-dimensional interferometric signals. These embodiments suppose that the natural movements of the sample are slow during the time of acquisition of the at least two two-dimensional interferometric signals. Typical acquisition time is 1-10 ms.

According to one or a plurality of embodiments, the method further comprises selecting in said temporal succession of two-dimensional interferometric signals acquired by the acquisition device, said at least two-dimensional interferometric signals having said phase shift, wherein the phase shift results from in vivo movements of the sample.

Here again, the natural movements of the in vivo sample are used for en face imaging, meaning that we take advantage of an effect that most of the methods try to eliminate or to overcome.

The different embodiments of the imaging method according to the first aspect of the present description can be combined with one another.

According to a second aspect, the present description relates to a system for in vivo, full-field interference microscopy imaging of a scattering three-dimensional sample, configured for implementing one or a plurality of embodiments of the method according to the first aspect.

According to one or a plurality of embodiments, the system according to the second aspect comprises:
- a full-field OCT imaging system for providing en face images of the sample, wherein said full-field OCT system comprises:
  - an interference device comprising an object arm intended to receive the sample and a reference arm comprising an optical lens and a first reflection surface, wherein said object arm and said reference arm are separated by a beam splitter and wherein the interference device is adapted to produce, when the sample is disposed on the object arm of the interference device, at each point of an imaging field, an interference between a reference wave obtained by reflection of incident light waves on an elementary surface of the first reflection surface corresponding to said point of the imaging field and an object wave obtained by backscattering of incident light waves by a voxel of a slice of the sample at a given depth, said voxel corresponding to said point of the imaging field,
  - an acquisition device configured to acquire a temporal succession of two-dimensional interferometric signals resulting from the interferences produced at each point of the imaging field, an OCT imaging system for providing at the same times of acquisition of said two-dimensional interferometric signals, cross-sectional images of both the sample and said first reflection surface of said full-field OCT imaging system;
- a processing unit configured to:
  - determine a plurality of en face images of a plurality of slices of the sample, each en face image being determined from at least two two-dimensional interferometric signals having a given phase shift;
  - determine from the cross-sectional images provided by the OCT imaging system at the times of acquisition of each of said two two-dimensional interferometric signals a depth for each en face image of said plurality of slices;
  - determine a 3D image of the sample from said plurality of en face images of said plurality of slices of the sample and depths.

The advantages stated for the imaging method can be transposed to the imaging system according to the second aspect of the present description.

According to one or a plurality of embodiments, said first reflection surface of the reference arm of the full-field OCT imaging system is position shifted to provide said optical path difference between said at least two-dimensional interferometric signals.

According to one or a plurality of embodiments, said first reflection surface of the reference arm of the full-field OCT imaging system is fixed and the processing unit is further configured to select in said temporal succession of two-dimensional interferometric signals acquired by the acquisition device, said at least two-dimensional interferometric signals having said given optical path difference, wherein the optical path difference results from in vivo movements of the sample.

According to one or a plurality of embodiments, said object arm of the full-field OCT imaging system further comprises an optical lens.

According to one or a plurality of embodiments, said optical lens of the reference arm and/or object arm is a microscope objective.

According to one or a plurality of embodiments, said reference arm and/or object arm of the full-field OCT imaging system can be moved with respect to said beam splitter of the interference device of said full-field OCT imaging system (along each optical axis of said reference arm and object arm).

According to one or a plurality of embodiments, the system further comprises a moving platform, wherein said full-field OCT imaging system and said OCT imaging system are mounted on said moving platform.

According to one or a plurality of embodiments, the OCT imaging system is a spectral domain OCT imaging system or a swept-source OCT imaging system, or a time-domain OCT imaging system.

The different embodiments of the imaging system according to the present description can be combined with one another.

Different features and embodiments of the various aspects of the present description can also be combined with one another.

BRIEF DESCRIPTION OF THE FIGURES

Other advantages and features of the imaging technique presented hereinabove will become apparent on reading the following detailed description, with reference to the figures in which:

FIG. 4A is an example of a cross-sectional image of the reference mirror (no sample visible) obtained using an exemplary OCT imaging system of an imaging system according to the present description and FIG. 4B represents the curve of variation of intensity along the vertical line of FIG. 4A;

FIG. 5A is an example of a cross-sectional image of the reference mirror (with cornea sample visible) obtained using an exemplary OCT imaging system of an imaging system according to the present description and FIG. 5B represents the curve of variation of intensity along the vertical line of FIG. 5A;

DETAILED DESCRIPTION

Systems

Figure 1A:
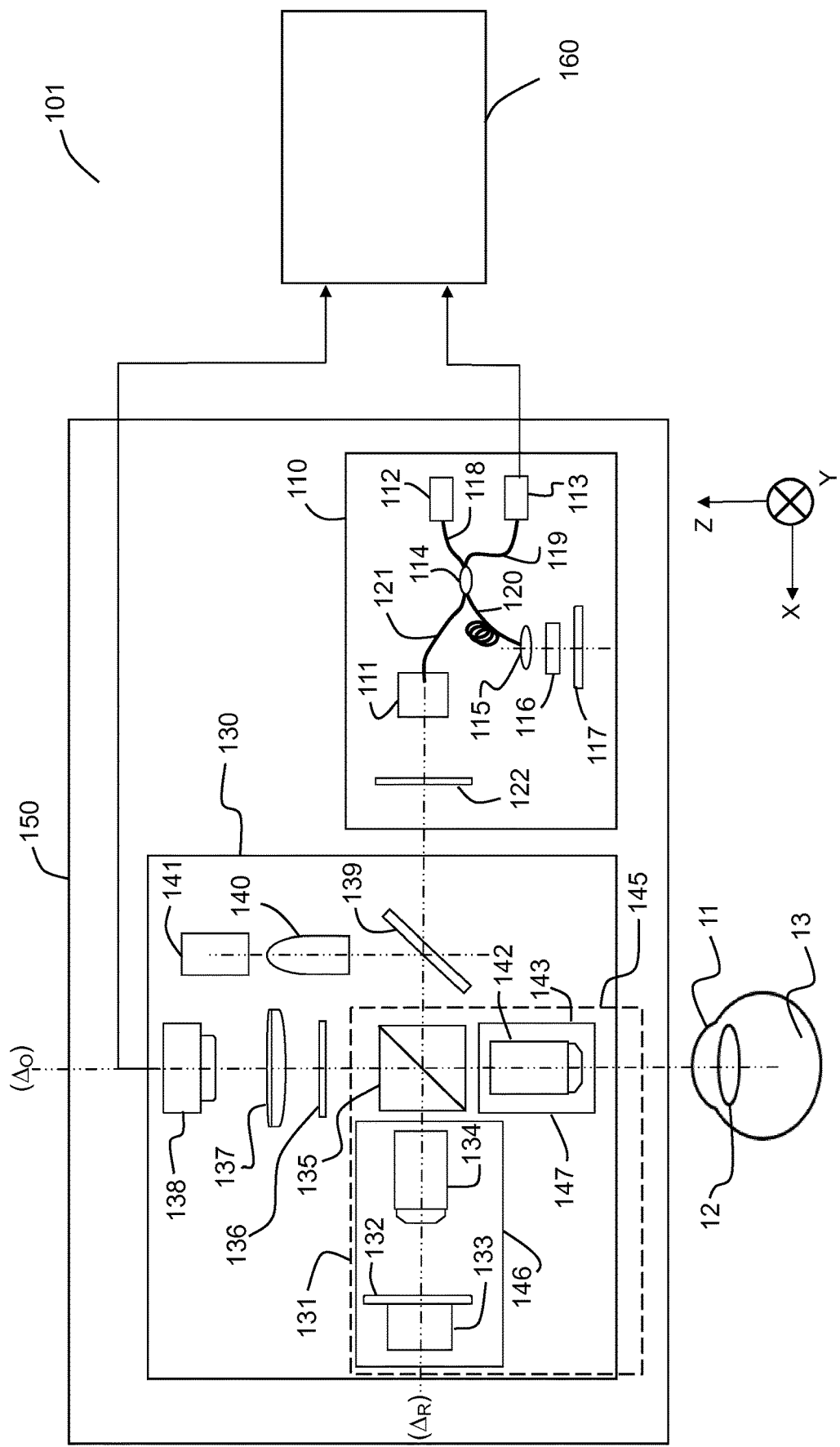
FIGS. 1A and 1B are schemes of systems according to embodiments of the present description.
Figure 1B:
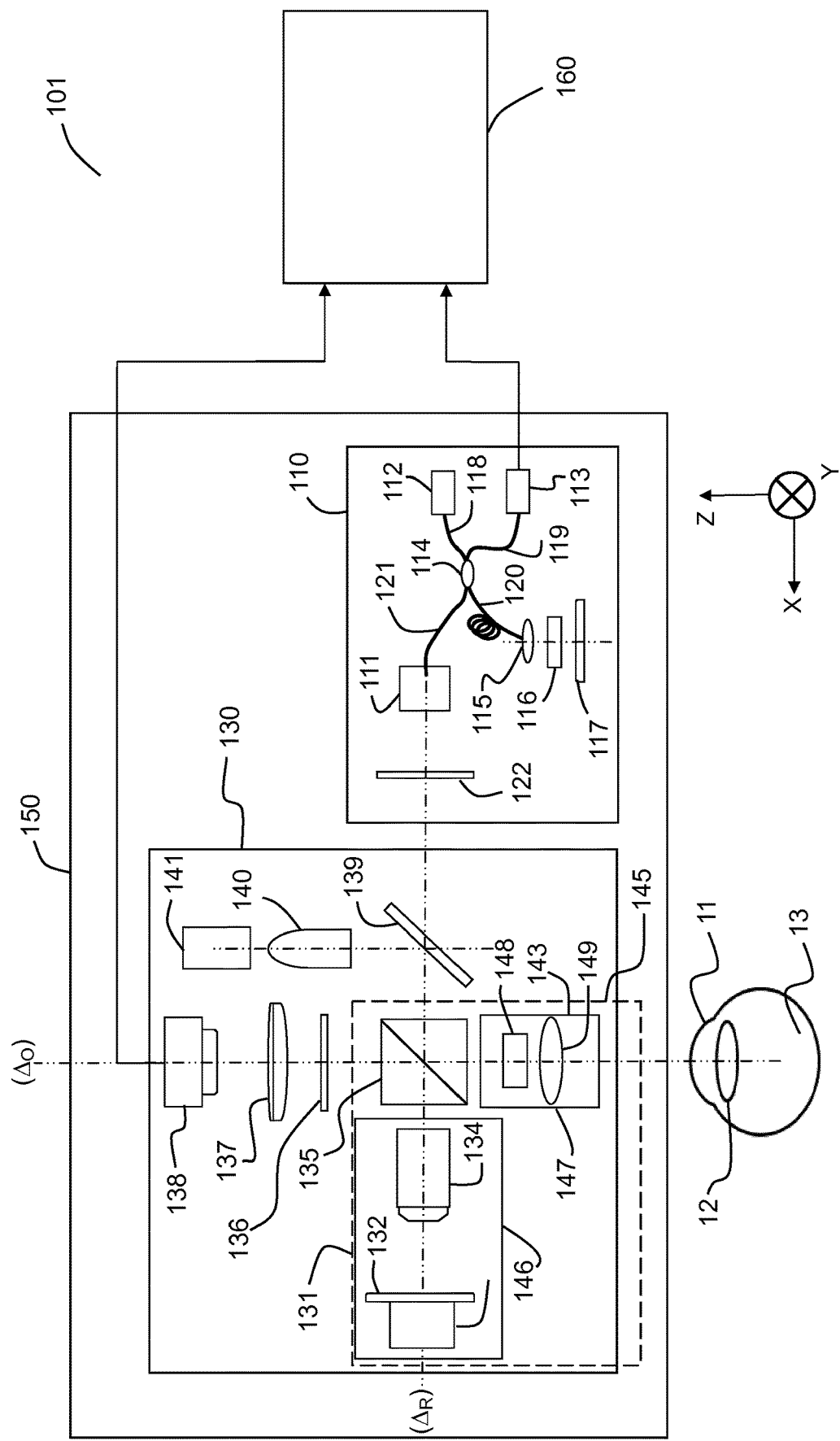

FIGS. 1A and 1B show respectively two embodiments 101, 102 of a system for in vivo, full-field interference microscopy imaging according to the present description.

The system 101 is suitable for implementing a method for 3D imaging of in vivo moving samples, and particularly, but not limited to, the anterior part 11 (cornea) of the in vivo eye. The system 102 is suitable for implementing a method for 3D imaging of in vivo moving samples, and particularly, but not limited to, the posterior part 13 (retina) of the in vivo eye.

The system 101 shown in FIG. 1A comprises two imaging systems, a full-field OCT ("FFOCT") imaging system 130 and an optical coherence tomography ("OCT") imaging system 110 and at least one processing unit 160. The FFOCT imaging system enables to get "en face" images of a moving in vivo sample 11, i.e. images of in-depth sections of the sample, and the optical coherence tomography ("OCT") imaging system 110 provides information about the position of the sample in an axial (Z) direction, e.g. along an optical axis. The system 101 may further comprise a moving platform 150, e.g. with one or several motors, on which the FFOCT imaging system 130 and the OCT imaging system 110 are mounted. The moving platform 150 is capable of translating jointly the FFOCT imaging system and the OCT imaging system in all X, Y and Z perpendicular directions.

The FFOCT imaging system 130 of FIG. 1A comprises an interference device 145 and an acquisition device 138 connected to said at least one processing unit 160.

According to one embodiment, the interference device 145 comprises a beam splitter element 135, for example a non-polarizing splitter cube, making it possible to form two arms, a reference arm 146 with optical axis $\Delta_R$, and an object arm 147 with an optical axis $\Delta_O$. In FIG. 1A, the optical axis $\Delta_O$ of the object arm defines the Z axis and the optical axis $\Delta_R$ of the reference arm defines the X axis. The reference arm 146 comprises a reflection surface 133. The reflection surface 133 may be flat; it is for example a metallic mirror, a neutral density (ND) filter glass, or simply a glass plate. The object arm 147 is intended to receive, in operation, the three-dimensional scattering sample 11, a volume of which it is a desire to produce a tomographic image.

In the embodiment of FIG. 1A, the reflection surface 133 is mounted on a piezo electric stage (PZT) 132 for phase modulation; such phase modulation may be used in one embodiment of the method according to the present description, and may not be used in another embodiment, as it will be described further.

The interference device is adapted to produce optical interferences between, on the one hand, reference waves obtained by reflection of light emitted by a light source 141, spatially incoherent or of low coherence length, by each elementary surface of the reflection surface 133 of the reference arm 146 and, on the other hand, of the object waves obtained by backscattering of the light emitted by the same source by each voxel of a slice of a sample 11 depth wise in the sample, the sample 11 being disposed on the object arm 147, said voxel and said elementary surface corresponding to the same point of the imaging field.

The light source 141 is a source that is spatially incoherent and of low temporal coherence length (in practice, in a range from 1 to 20 micrometers), for example a thermal light source (e.g. halogen lamp) or a LED. According to one or more exemplary embodiments, the light source 141 can form part of the FFOCT imaging system 130, as in the example of FIG. 1A, or can be an elemental external to the imaging system, the FFOCT imaging system 130 being configured to work with light waves emitted by the source. An optical system 140 may be used to realize a Kohler-like illumination. In operation, light emitted by the light source 141 is reflected by a dichroic mirror 139 and reaches beam-splitter element 135 of the interference device 145.

The acquisition device 138 allows the acquisition of at least one two-dimensional interferometric signal resulting from the interferences between the reference waves and the object waves.

The acquisition device 138 is for example an image sensor, of CCD (Charge-Coupled Device) or CMOS (Complementarity metal-oxide-semiconductor) camera type. This acquisition device is capable of acquiring images at a high rate, for example with a frequency comprised between 100 Hz and 1000 Hz, or higher. Depending on the dynamics of the sample studied, and more specifically the dynamics of the movements within the sample, it is possible to use the cameras operating from a few Hz up to several KHz.

The processing unit 160 is configured to execute at least one step of processing of at least one two-dimensional interferometric signal acquired by the acquisition device 138 and/or at least one step of image generation in accordance with at least one of the imaging methods according to the present description, in order to generate at least one image of the sample slice.

In one embodiment, the processing unit 160 is a computing device comprising a first memory CM1 (not represented) for the storage of digital images, a second memory CM2 (not represented) for the storage of program instructions and a data processor, capable of executing program instructions stored in this second memory CM2, in particular to control the execution of at least one step of processing of at least one two-dimensional interferometric signal acquired by the acquisition device 138 and/or at least one step of image computation in accordance with at least one of the imaging methods according to the present description.

The processing unit can also be produced in integrated circuit form, comprising electronic components suitable for implementing the function or functions described in this document for the processing unit. The processing unit 160 can also be implemented by one or more physically distinct devices.

In the example of FIG. 1A, the interference device is a Linnik interferometer and comprises two optical lenses 134, 142, e.g. microscope objectives, arranged on each of the reference and object arms. The microscope objectives 134, 142 may have a relatively high numerical aperture (typically ~0.3), which at the same time provides relatively large field-of-view (typically ~1 mm). The reflection surface 133 is thus located at the focus of the objective 134 of the reference arm and the sample 11 is intended to be positioned at the focus of the objective 142 of the object arm; more specifically, the layer of interest of the sample is intended to be positioned at the focus of the objective 142. Other types of interferometers can be envisaged for the implementation of the methods according to the present description, and in particular but without limitation Michelson interferometers.

In the example of FIG. 1A, the microscope objective 142 of the object arm 147 is mounted on a motorized platform 143, movable along the direction of an optical axis of said object arm (Z axis), i.e, closer or further from the sample 11. Both the reflective surface 133 and microscope objective 134 of the reference arm 146 are mounted on another motorized platform 131, which can move along the direction of an optical axis of said reference arm (X axis).

At the output of the interferometer 145, there may be an optical spectral filter 136 and an optic lens 137, for example an achromatic doublet, whose focal length is adapted to allow a suitable sampling of the sample 11 by the acquisition device 138, and which makes it possible to conjugate the planes situated at the foci of the two objectives and a detecting surface of the acquisition device 138. The acquisition device 138 thus acquires the interference signals produced by the interference device. In order to not limit the resolution permitted by the microscope objectives 134 and 142, the choice of the focal length of the optic 137 will be in line with the Shannon sampling criterion. The focal length of the optic 137 is for example a few hundreds of millimeters, typically 300 mm.

The optical spectral filter 136 advantageously transmits the wavelengths of the light source 141, while blocks the wavelengths of the OCT source 112, as further described below.

Glass plates or, so called dispersion compensation blocks (not represented in FIG. 1A), may be provided on each of the arms to compensate the dispersion.

The OCT imaging system 110 comprises a spatially coherent light source 112, a detector 113 and an interference device with a beam splitter element 114 that defines a reference arm and an object arm of the interference device of the OCT imaging system. Typically, the spatially coherent light source 112 can be a superluminescent diode (SLD), for example in case of Spectral-Domain OCT or Time-Domain OCT, or a swept laser source. Typically, the detector 113 can be a device directly converting incident optical power into an electrical signal, for example a photodiode, in case of Time-Domain-OCT or Swept-source OCT, or a spectrometer, in case of Spectral-Domain OCT.

The light from the source 112 is collimated into a fiber 118 and is split by the beam splitter element 114 into two fibers 121 (object arm) and 120 (reference arm). In operation, after going through the fiber 120, light passes through a lens 115, a dispersion compensation plate 116, which can be rotated, and reaches a reflecting surface 117, for example a metalized mirror. After going through the fiber 121, light reaches a transverse scanning mechanism 111, which can scan the beam in 2D (X-Y) directions. Then light beam passes though an optical filter 122, passes though the dichroic mirror 139 and is split into the FFOCT reference arm 146 and the FFOCT sample arm 147 by the beam splitter 135.

Optical filter 122 is chosen in order to allow a light beam issued from the OCT source 112 to propagate in both the OCT reference arm, the FFOCT reference arm and the FFOCT sample arm but to block light from the FFOCT source 141; on the other hand, optical filter 136 blocks the light beam issued from the OCT source 112 and pass the light from the FFOCT source.

Figure 1C:
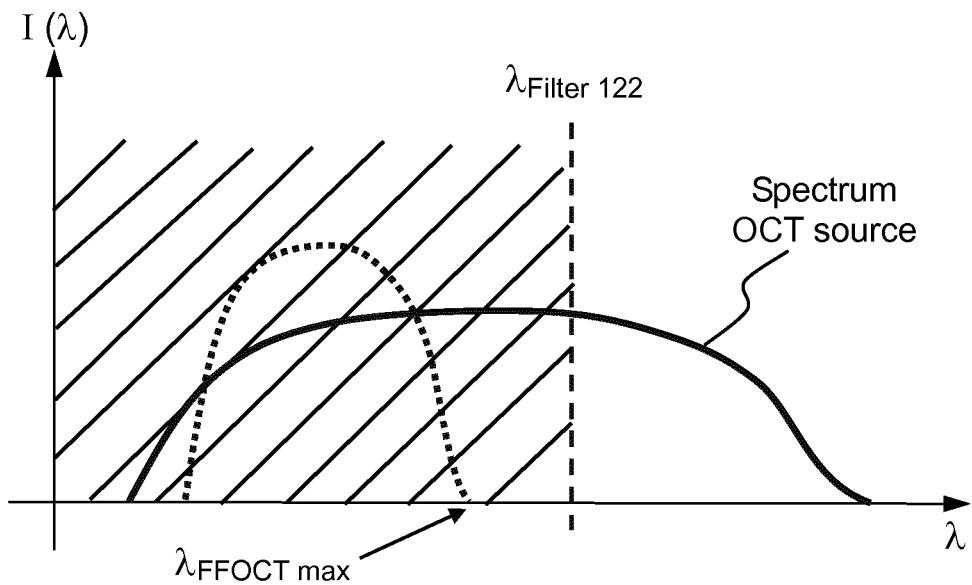
FIGS. 1C and 1D show exemplary light sources spectra of the OCT source and the FFOCT source and blocking parts of such spectra with filters of the system, according to embodiments of the present description.
Figure 1D:
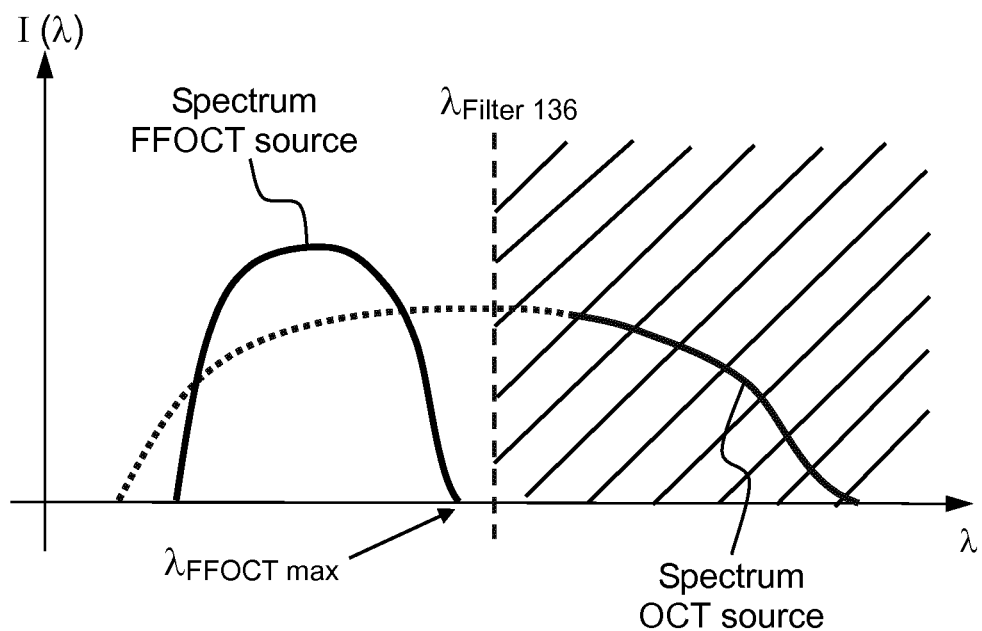

Functionalities of the optical filters 122 and 136 are further described in relation with FIGS. 1C, 1D. In the example shown in FIG. 1C, the optical filter 122 may block (dashed lines) wavelengths of the OCT light source 112 that are below a given wavelength $\lambda_{Filter122}$ which is above the highest wavelength $\lambda_{FFOCTmax}$ used in the FFOCT imaging system. On the other hand, as illustrated in FIG. 1D, optical filter 136 in the FFOCT imaging system may block wavelengths of the OCT light source which are above a given wavelength $\lambda_{Filter136}$ which is above said highest wavelength $\lambda_{FFOCTmax}$ used in the FFOCT imaging system. As a result, none of the OCT light reaches the acquisition device 138.

Obviously, FIGS. 1C and 1D only represent an example of functionalities of the optical filters 122, 136. Many other configurations are possible as long as none of the OCT light reaches the acquisition device 138.

In a preliminary step, the optical pathlength of the OCT arm from the beam splitter 114 to the mirror 117 (reference arm) may be matched with the optical pathlength from the beam splitter 114 to the mirror 133 in the FFOCT reference arm 146. Matching of the optical pathways of the OCT and FFOCT reference arms may be achieved in a simple way. In real time, we look at the OCT images. If the mirror of the FFOCT reference arm is not visible on the OCT images, then reference arms of OCT and FFOCT systems are not matched. We extend the reference arm of the OCT imaging system until the mirror of the FFOCT reference arm is visible on the OCT images.

In operation, back-reflected light from the reflecting surface 133 in the reference arm 146 of the FFOCT imaging system combines at the beam splitter 135 with the back-reflected light from the different layers of the sample. Beam splitter 135 again divides the light into two parts: the reflected part is blocked by the filter 136 (as explained in relation with FIG. 1D) and the transmission part passes though the dichroic mirror 139, filter 122, fiber 121. Then this light beam mixes with the back-reflected light coming from the fiber 120 and, after passing through the fiber 119, is collected by the detector 113. The detector 113, for example a spectrometer, is configured to record the, so called, A-scan—a 1D profile, containing information about the reflectivity at different depths of the imaged object. Further, it collects information about the position of the reference mirror 133 of the reference arm 146 of the FFOCT imaging system. By scanning the beam with the scanning mechanism 111, it is possible to acquire 2D and 3D reflectivity images.

The OCT imaging system may be a Spectral-Domain OCT (the detector 113 is a spectrometer) but it can be also a Time-Domain OCT or a Swept-Source OCT.

The OCT imaging system may also provide information about the speed of the sample, based on several consecutive positions of the sample and the time interval between them. Information about the instantaneous speed of the sample can be useful to predict its future movement (e.g. if the sample in the first moment is moving in a rapid way in Z direction, we can expect that in the next moment it will continue to move in the same direction).

As it will be further explained below, embodiments of the method according to the present description use the above-mentioned OCT imaging system for obtaining information about the positions of the different layers of interest of the sample 11 and the position of the reference mirror 133 of the reference arm 146 of the FFOCT imaging system.

The system 102 shown in FIG. 1B is similar to that of FIG. 1A with minor differences. In the embodiment of FIG. 1B, the role of the microscope objective in the sample arm 147 of the FFOCT imaging system is performed by the cornea 11 and the lens 12 of the eye. Additionally, an adaptive lens 148, for example a liquid lens, and a rotating glass plate 149 may be inserted in the reference arm to compensate for the aberrations and the dispersion mismatch introduced by the eye. Due to the typically large depths of focus of the lens 12 of the eye, imaging of retinal layers of different depths can be performed without correcting for defocus and, therefore, without moving the reference arm 146, contrary to the device shown in FIG. 1A. In all the other aspects, the system may be similar to that of the embodiment shown in FIG. 1A.

3D Imaging Methods

Figure 2A:
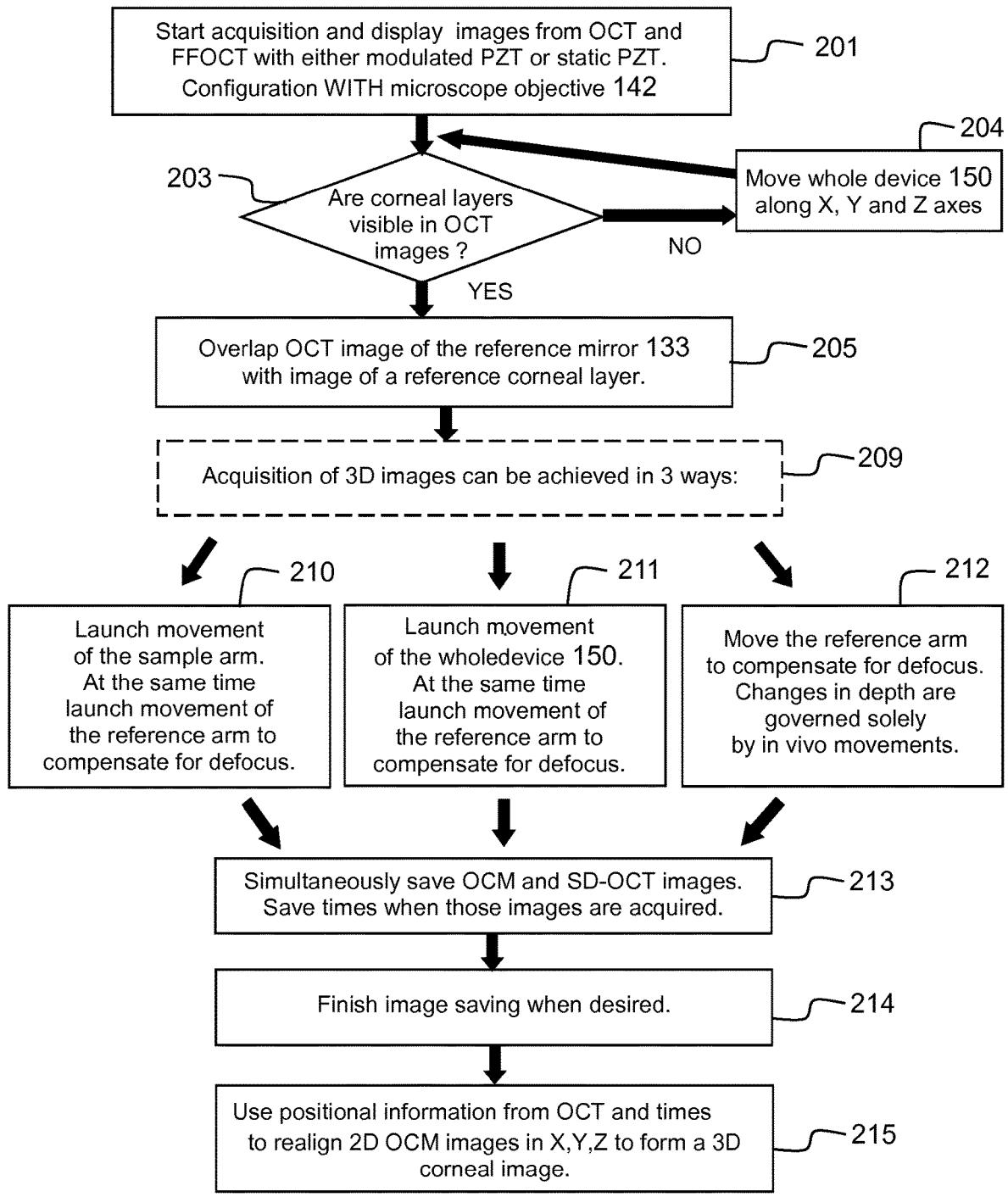
FIGS. 2A, 2B are flow diagrams of embodiments of an imaging method according to the present description and images to illustrate steps of some of these embodiments.

FIG. 2A is a flow diagram of embodiments of an imaging method according to the present description. It can be implemented using a system as shown in FIG. 1A for example. The described methods are suitable for 3D imaging of in vivo moving samples, and particularly, but not limited to, the anterior part 11 (cornea) of the in vivo eye.

Figure 2B:
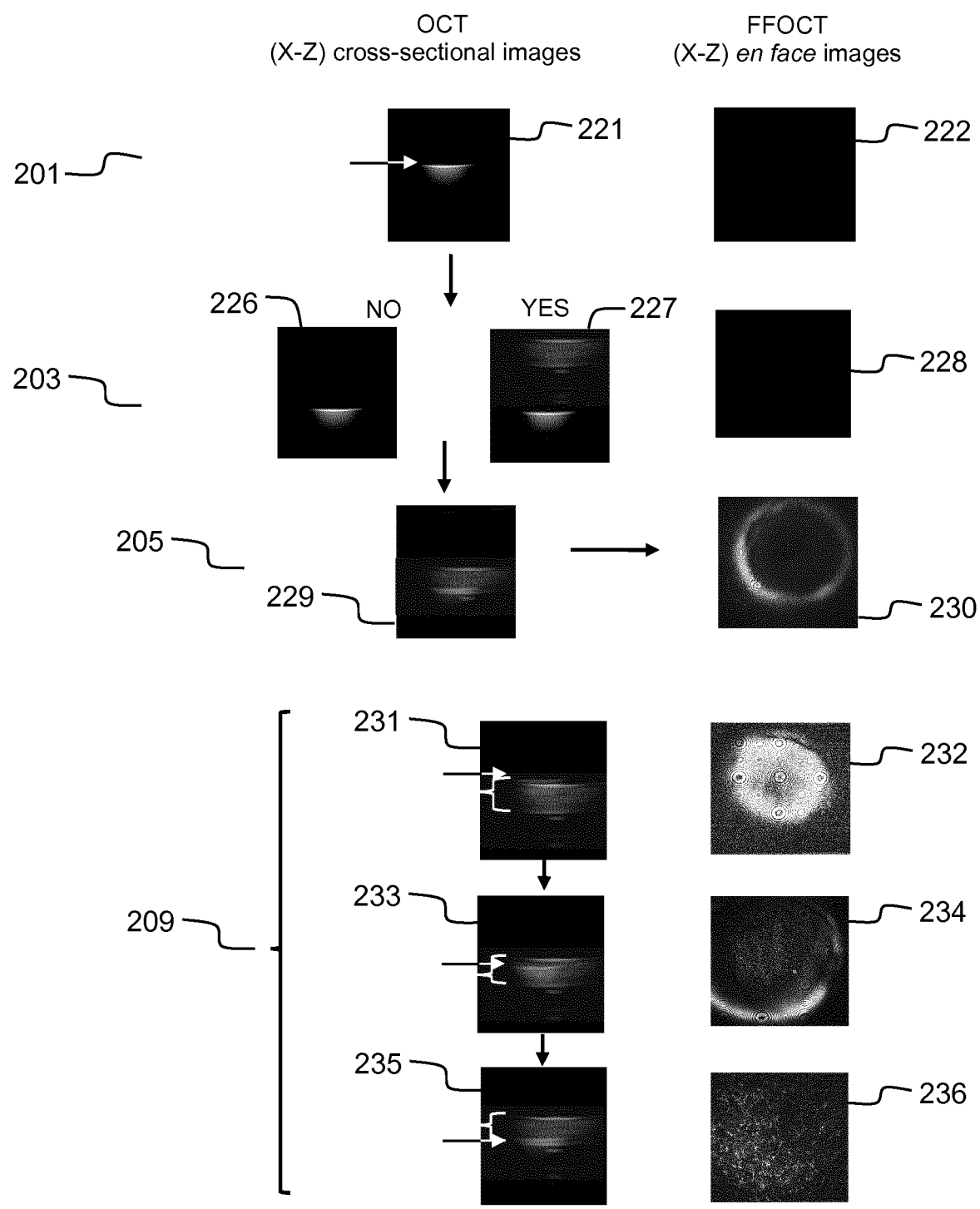

FIG. 2B illustrates images acquired both by the OCT imaging system and the FFOCT imaging system during the different steps shown in FIG. 2A.

Steps of FIGS. 2A, 2B illustrate acquisition of 3D images.

In step 201, images from the two devices, the OCT imaging system and the FFOCT imaging system, are obtained and displayed. FFOCT images can be obtained with either modulated PZT or static PZT, as it will be described further. In corresponding step 201 in FIG. 2B, OCT image 221 shows the mirror 133 of the reference arm of the FFOCT imaging system. On images 222 and 228 there is only the camera noise because defocus correction is not performed yet or/and optical pathways of the sample and reference arms are not matched.

In step 203, it is checked whether the corneal layers are visible in the OCT images.

If NO, as shown in image 226 of FIG. 2B, the whole device 150 may be moved along X, Y and Z axes (step 204). For example, it can be moved by an operator until the required layers are observed on the screen.

If YES, as shown in image 227 of FIG. 2B, the OCT image of the reference mirror 133 may be overlapped with a corneal layer (the reference corneal layer) by moving the whole device 150 along X and Z axes (step 205). The reference corneal layer may be any layer, although, typically, a layer providing a bright peak may be chosen. In FIG. 2B, image 229 shows the image of the reference mirror that overlaps the image of a reference corneal layer. At the same time, a fuzzy FFOCT image 230 can be seen because of lack of defocus correction.

A FFOCT image solely does not contain information about the location in the sample, where the image was captured. OCT imaging system 110, used in combination with FFOCT bridges this gap by providing X,Y,Z coordinates of the captured image. Stack of 2D FFOCT images each accompanied with their locations can be grouped to form a 3D image. More precisely, the method of 3D image acquisition 209 is described below.

In a first implementation (210), only the microscope objective 142 is moved by the motor below the sample arm 147. At the same time the reference arm 146 is moved further from (or closer to) the beam splitter 135 to compensate for the optical path mismatch between the sample arm 147 and the reference arm 146.

In the second implementation (211), the whole device 150 is moved by the motor 101 closer to (or further from) the sample 11. At the same time the reference arm 146 is moved further from (or closer to) the beam splitter 135 to compensate for the optical path mismatch between the sample arm 147 and the reference arm 146.

In the third implementation (212), only the reference arm 146 is moved further from the beam splitter 135 to compensate for the optical mismatch (defocus) between the sample arm 147 and the reference arm 146. Extent of the reference arm movement depends on the instantaneous sample position (or depth in the sample). Changes in the sample position (or depth) are governed solely by in vivo sample movements.

In all implementations, individual en face images of slices at different depths in the sample are recorded according the methods described below. At the same time the position (X, Y, Z) of the slice corresponding to each 2D image is recorded by the OCT imaging system 110. By having the position information for each 2D image, 2D images can be repositioned in order to form a 3D image.

Determination of the depth of each slice for which an en face image is acquired is made by storing (213) the times when those images are acquired. Acquisition is stopped when desired (214). In step 215, we use the positional information from OCT images at the different times that have been stored to realign 2D OCM images, i.e. images obtained by the FFOCT device and form a 3D corneal image.

Examples of 2D cross-section images and a 1D images (A-scans) used for position detection are shown in FIG. 4A, 4B and FIG. 5A, 5B.

FIGS. 4A, 4B, 5A, 5B illustrate how the OCT imaging system is used to determine the depth of a slice that is imaged by the FFOCT imaging device. It also shows the compensation for defocus.

FIGS. 4A and 4B show respectively the 2D cross-sectional image and corresponding profile (A-scan) obtained using the OCT imaging system when the sample is not introduced. FIGS. 5A and 5B show respectively the 2D cross-sectional image and corresponding profile obtained using the OCT imaging system when the sample is introduced in the sample arm and is within the field of view of the OCT imaging device. The depth of a slice is measured relatively to the non-defocus corrected position of a reference, corresponding to a black vertical line at 0 depth in FIGS. 4A, 4B, 5A, 5B). For example, a reference layer is the top layer of the cornea.

On image 231 the very top layer of the cornea (cornea is shown in bracket) overlaps with the reference mirror (shown by an arrow). This position corresponds to the "0" position in FIGS. 4A, 5A, i.e. when the difference between the corneal top layer position and the non-defocus corrected reference mirror position equals zero. As a result, no defocusing correction is applied and we get the image of the corneal surface 232.

On image 233, the corneal top layer is shifted up (on the image) relatively to the non-defocus corrected reference arm position. As a result, a non-zero depth is measured. Based on this depth, reference arm is shifted down (on the image) from the non-defocus corrected reference position. As a result, we get image 234 from the corneal layer, which in OCT image overlaps with the reference mirror image.

On image 235 everything is repeated as in the step before. Cornea is shifted up again and reference arm with mirror is shifted down again, as a result providing us with the FFOCT image from the deep cornea 236.

The embodiments described above are proposed to be used for imaging in vivo moving samples and, particularly, the anterior part of the in vivo eye.

Figure 3A:
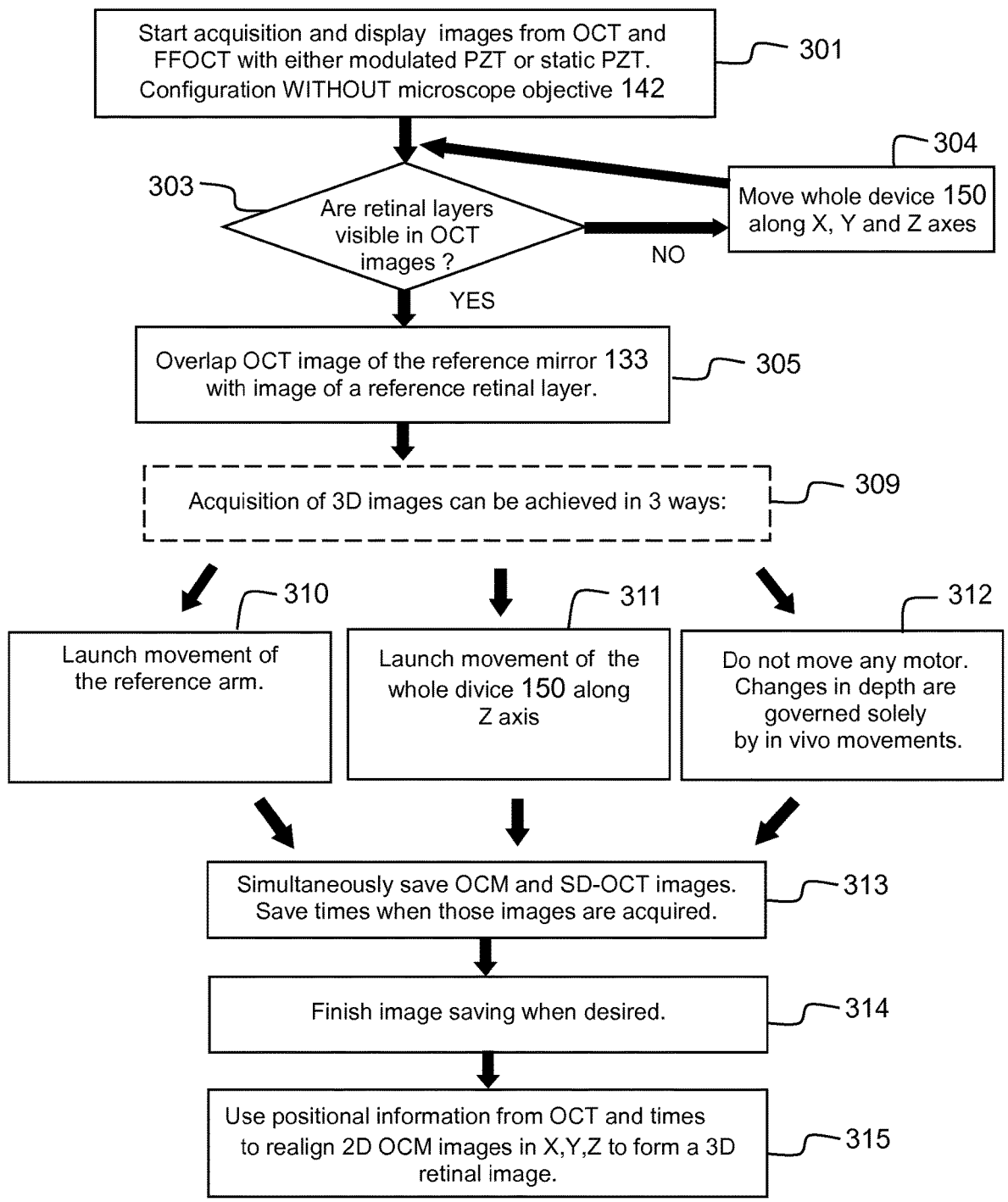
FIGS. 3A, 3B are flow diagrams of further embodiments of an imaging method according to the present description and images to illustrate steps of some of these embodiments.

Embodiments of the method described below can also be used for imaging various in vivo samples, but the focus is, particularly, on the posterior part of the in vivo eye. FIG. 3A is a flow diagram of embodiments of an imaging method according to the present description. It can be implemented using a system as shown in FIG. 1B for example. The described methods are suitable for imaging of in vivo moving samples, and particularly, but not limited to, the posterior part 13 (retina) of the in vivo eye.

Figure 3B:
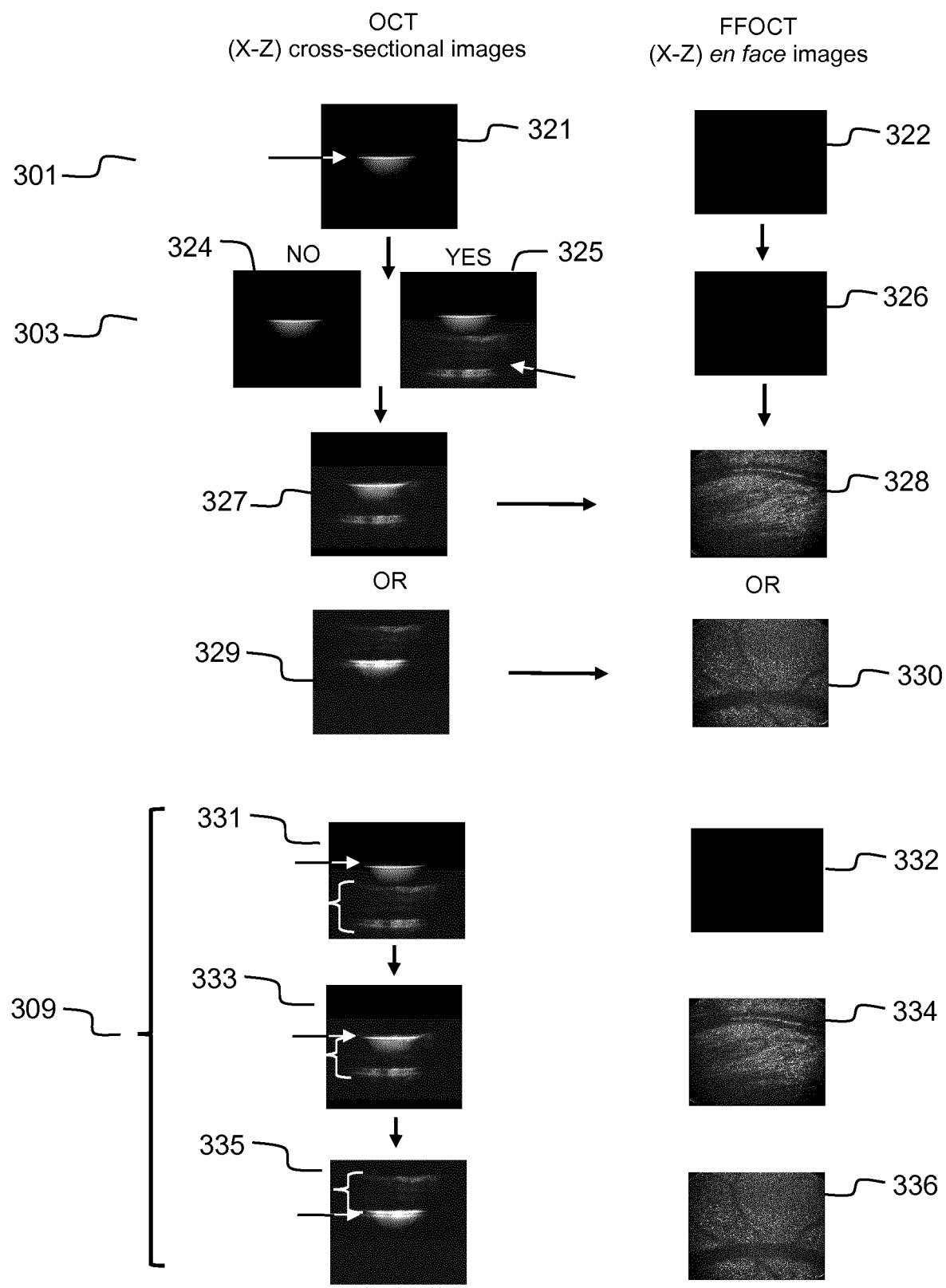

FIG. 3B illustrates images acquired both by the OCT imaging system and the FFOCT imaging system during the different steps shown in FIG. 3A.

In step 301, acquisition starts (Acquisition comprises the processing to obtain images) and images are displayed from the two devices, the OCT imaging system and the FFOCT imaging system. FFOCT acquisition can be done with either modulated PZT or static PZT, as described below. In step 303, it is checked whether the retinal layers are visible in the OCT images. On images 322 and 326 there is only the camera noise because defocus correction is not performed yet or/and optical pathways of the sample and reference arms are not matched.

If NO, as shown in image 324 of FIG. 3B, the whole device 150 is moved along X, Y and Z axes (step 304). If YES, as shown in image 325 of FIG. 3B, the OCT image of the reference mirror 133 is overlapped with the retinal layer of interest by moving the whole device 150 along X, Y and Z axes (step 305).

At that stage, optical path length is matched between mirror 133 and any of the retinal layers, as illustrated in OCT images 327 or 329, FIG. 3B and corresponding FFOCT images 328, 330.

Then, 3D image acquisition 309 is started.

In a first implementation (310), only the reference arm 146 is moved by the motor below.

In a second implementation (311), the whole device 150 is moved by the motor 101 closer to (or further from) the sample 11.

In a third implementation, none of the motors are moved and creation of the 3D stack is achieved by the in vivo movements of the sample.

As for FIGS. 2A, 2B, individual 2D cross-sectional images of the moving in vivo sample are recorded according to the mentioned above method. Device may be adjusted to get the maximum FFOCT signal on the frequencies of the typical sample movements, if in vivo movements of the sample are used. At the same time the position (X, Y, Z) of the sample corresponding to each 2D image is recorded by the OCT imaging system 110 (steps 313, 314, 315 and corresponding images 331—336 on FIG. 3B). By having the position information for each 2D image, 2D images can be repositioned in order to form a 3D image.

Determination of En Face Images

In order to extract an FFOCT image from the direct camera images a phase-shifting scheme is required.

In a first embodiment of the present description, a standard FFOCT image retrieval method is used, according to which phase-shifting is provided by modulating the piezo element (PZT) 132. This embodiment is useful for the case of slowly moving samples (their movement during the typical time of image acquisition should be $\ll\pi$ phase shift) or for the fast-moving samples in the moments of no movements. FFOCT image can be extracted from the 2, 4 or 5 direct images depending on the scheme.

For example, for 2 direct images:

$$I(x, y) = \frac{I_0}{4} \cdot \{R_{inc}(x, y) + R_{ref}(x, y) + 2 \cdot \sqrt{R_{sam}(x, y) \cdot R_{ref}(x, y)} \cdot \cos[(\phi(x, y) + \Psi]\}$$

Where:
- $\phi$ is the phase difference between the sample signal and the reference signal;
- $\psi$ is the phase shift induced by PZT
- $I_0$ is the photon flux of the illumination;
- $R_{ref}(x, y) \approx$ const is the reflectivity of the reference, which is spatially uniform;
- $R_{sam}(x, y)$ is the reflectivity of the sample structures within the coherence volume, which is the plane of interest;
- $R_{inc}(x, y)$ is the reflectivity of all the other structures that are out of the coherence volume and other stray reflections.

Two phase-shifted images are:

$$I_1(x, y) = \frac{I_0}{4} \cdot \{R_{inc}(x, y) + R_{ref}(x, y) + 2 \cdot \sqrt{R_{sam}(x, y) R_{ref}(x, y)} \cdot \cos[\phi(x, y) + 0]\}$$

$$I_2(x, y) = \frac{I_0}{4} \cdot \{R_{inc}(x, y) + R_{ref}(x, y) + 2 \cdot \sqrt{R_{sam}(x, y) \cdot R_{ref}(x, y)} \cdot \cos[\phi(x, y) + \pi]\}$$

By subtracting the two images and taking the module we get the FFOCT image or "FFOCT signal".

$$|I_1(x, y) - I_2(x, y)| = |I_0 \cdot \sqrt{R_{sam}(x, y) \cdot R_{ref}(x, y)} \cdot \cos[\phi(x, y)]|$$

Having a phase-shift between the two consecutive direct camera frames equals $\pi$ (in a 2-phase-shifting scheme) enables to get the highest possible FFOCT signal.

In a second embodiment of the present description, the image retrieval method used relies on the in vivo natural movements of the sample.

The applicants have shown that in ophthalmic tissue imaging applications, for example, natural eye movements introduce phase changes between consecutive direct images, which can be large enough to extract a FFOCT image. More precisely, applicants have measured the movements of the in vivo human eye and have shown that, when camera exposure time is set, for example, in a range of 1 ms to 10 ms (i.e. two consecutive camera frames are acquired in 2-20 ms, respectively), the eye movements induced phase shift between the consecutive camera frames can take any value from 0 to ±30 radians (or, equivalently, ±10π). More generally, in vivo movements may induce phase changes between the consecutive direct camera images. These phase changes can be used to extract the FFOCT image. According to this method FFOCT image can be extracted from the 2, 4 or 5 direct images, but not restricted to this sequence, depending on the scheme. Below, we will give example of FFOCT extraction method for the 2 direct images, however this invention is not limited to 2 images scheme only, instead it is applicable to every FFOCT image retrieval scheme.

When the sample is moving along the Z direction, the phase of the interference of the sample beam and the reference beam changes by a random amount $\psi$. Different phase shifts may happen during the time that camera acquires an image. In the simplest case, it can be considered that each camera image has an average phase $\langle \psi \rangle$. Then the recorded signal of the direct image on the camera is given by:

$$I(x, y) = \frac{I_0}{4} \cdot \{R_{inc}(x, y) + R_{ref}(x, y) + 2 \cdot \sqrt{R_{sam}(x, y) \cdot R_{ref}(x, y)} \cdot \cos[\phi(x, y) + \langle\psi\rangle]\},$$

Where:
- $\phi$ is the phase difference between the sample signal and the reference signal;
- $\langle \psi \rangle$ is the random phase shift induced by the natural movements of the in vivo sample. It is averaged over the acquisition time.
- $I_0$ is the photon flux of the illumination;

$R_{ref}(x, y) \approx$ const is the reflectivity of the reference, which is spatially uniform;

$R_{sam}(x, y)$ is the reflectivity of the sample structures within the coherence volume, which is the plane of interest;

$R_{inc}(x, y)$ is the reflectivity of all the other structures that are out of the coherence volume and other stray reflections.

Then the two direct images are:

$$I_1(x, y) = \frac{I_0}{4} \cdot \{R_{inc}(x, y) + R_{ref}(x, y) + 2 \cdot \sqrt{R_{sam}(x, y) \cdot R_{ref}(x, y)} \cdot \cos[\phi(x, y) + \langle 0 \rangle]\}$$

$$I_2(x, y) = \frac{I_0}{4} \cdot \{R_{inc}(x, y) + R_{ref}(x, y) + 2 \cdot \sqrt{R_{sam}(x, y) \cdot R_{ref}(x, y)} \cdot \cos[\phi(x, y) + \langle \psi \rangle]\}$$

By subtracting two images and simplifying the formula we get:

$$I_1(x, y) - I_2(x, y) = \frac{I_0 \cdot \sqrt{R_{sam}(x, y) \cdot R_{ref}(x, y)}}{2} \cdot \left[\frac{\sin\phi \cdot \sin(\langle \psi \rangle)}{2} + \cos\phi \cdot \sin^2\left(\frac{\langle \psi \rangle}{2}\right)\right]$$

From the formula, it can be seen that the FFOCT image can be obtained for every average phase difference $\langle \psi \rangle$ for the two consecutive or more distant camera frames, but maximum FFOCT signal is achieved for $\langle \psi \rangle = \pi$ (considering that $\phi=0$).

Figure 6:
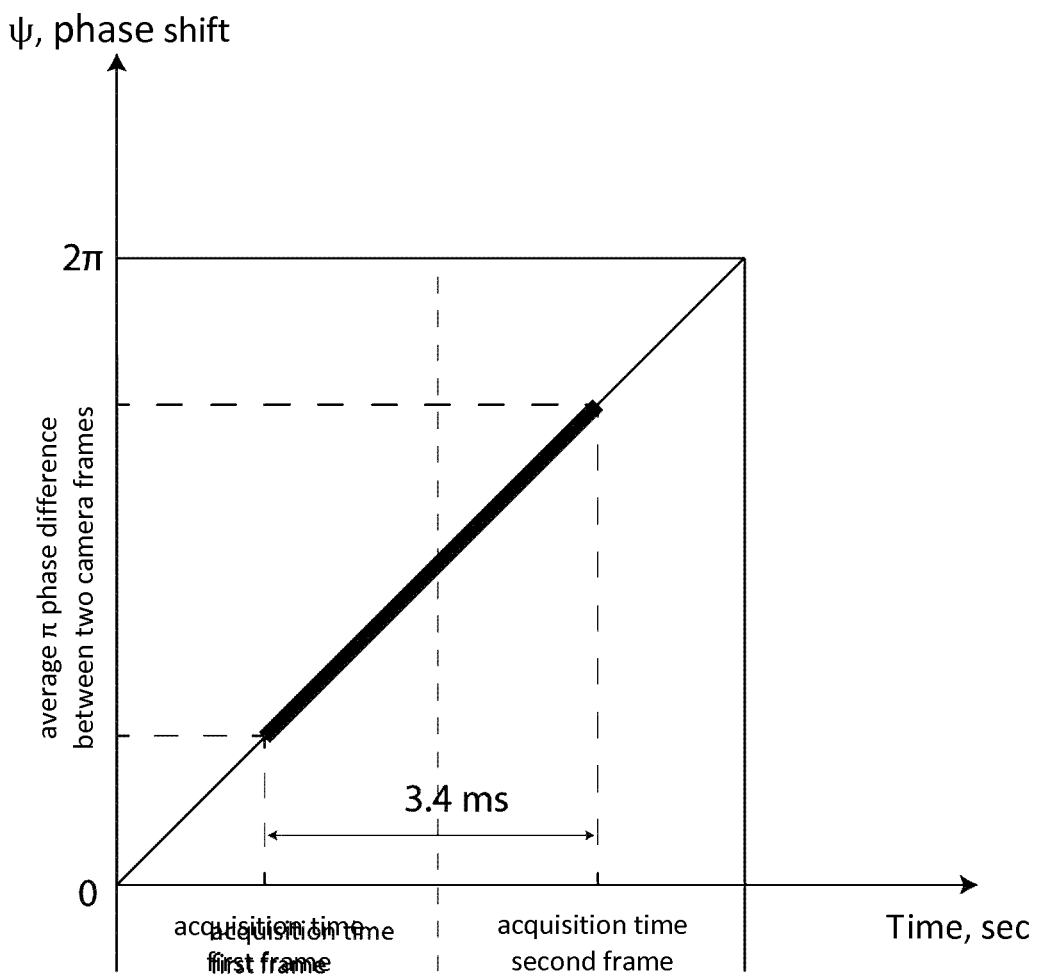
FIG. 6, is a graph illustrating required phase-shifting by the in vivo movements.

In FIG. 6, it is shown, that in order to get high FFOCT signal, not only the phase shift needs to be large enough, but also that it should happen during the time, while camera acquires several frames (in FIG. 6 an example of 2 frames is shown). By knowing the instantaneous speed of the in vivo movements of the sample, one can find the time interval that is needed to achieve the average $\pi$ phase shift. Stack of the direct images may be recorded and the two frames, corresponding to the $\pi$ phase shift, can be extracted from the stack and processed in order to get a high FFOCT signal. This method can be, for example, used for eye imaging: when the movement of the eye is such that the induced phase shift between the two consecutive direct camera images is smaller than a radian (typically out of the large spikes liked to heart beat) then the phase-shift between these two images is sufficient to obtain an FFOCT image. Additionally, in order to increase the number of useful (with $\pi$ phase shift) direct images of the camera, one can adjust the camera acquisition speed and the wavelength of the light source according to the typical speeds of in vivo sample movements. Speed of the sample, at which the maximum FFOCT signal is achieved:

$$v = \frac{\lambda \cdot \langle \psi \rangle}{2 \cdot \pi \cdot T}$$

Where:

$\lambda$ is the wavelength of the FFOCT light source.

T is the time that takes the camera to acquire two direct images

From the formula it follows that by initially knowing the typical speed of the sample in vivo movements v, we can adjust the camera speed and the wavelength of the light source to get the average $\pi$ phase difference between the direct images (and therefore the best FFOCT signal) at the typical speed of the sample. When the movement of the eye is such that the induced phase shift between two successive images is smaller than a radian (typically out of the large spikes liked to heart beat) two phase image of standard FFOCT is usable.

Previously, for simplicity purposes, it was considered that each camera image has an average phase $\langle \psi \rangle$. It is possible to make a more comprehensive analysis by considering the phase at each moment of time $\psi(t)$ and considering that camera acquires the image by integrating the light during an exposure time (for example, from time $T_0$ to time $T_1$).

$$I(i, y) = \frac{I_0}{4} \cdot \left\{ R_{inc}(x, y) + R_{ref}(x, y) + 2 \cdot \sqrt{R_{sam}(x, y) \cdot R_{ref}(x, y)} \cdot \int_{T_0}^{T_1} \cos[\phi(x, y) + \psi(t)] \right\}$$

Then the two consecutive direct images are:

$$I_1(x, y) = \frac{I_0}{4} \cdot \left\{ R_{inc}(x, y) + R_{ref}(x, y) + 2 \cdot \sqrt{R_{sam}(x, y) \cdot R_{ref}(x, y)} \cdot \int_{T_0}^{T_1} \cos[\phi(x, y) + \psi(t)] dt \right\}$$

$$I_2(x, y) = \frac{I_0}{4} \cdot \left\{ R_{inc}(x, y) + R_{ref}(x, y) + 2 \cdot \sqrt{R_{sam}(x, y) \cdot R_{ref}(x, y)} \cdot \int_{T_1}^{T_2} \cos[\phi(x, y) + \psi(t)] dt \right\}$$

By subtracting the two images and simplifying the formula we get:

$$I_1(x, y) - I_2(x, y) = const \cdot \left[ \int_{T_0}^{T_1} \cos[\phi(x, y) + \psi(t)] dt - \int_{T_1}^{T_2} \cos[\phi(x, y) + \psi(t)] dt \right]$$

The applicants have measured the function $\psi(t)$ for in vivo human eye and shown that high FFOCT signal can be reached for different camera exposure times (for example, 1 ms-10 ms).

In the example of FIG. 6, in order to obtain FFOCT image we need to acquire at least two direct images, which have an average phase shift between them equal to $\pi$ (Y axis on the graph). If we know the average moving speed of the sample, we know the time that is needed for sample to move by 7E (for example 3.4 ms, how it is shown on the graph). Then we can adjust the camera acquisition speed to acquire two images in 3.4 ms time. As a result, phase-shifting is performed by the sample only.

Figure 7:
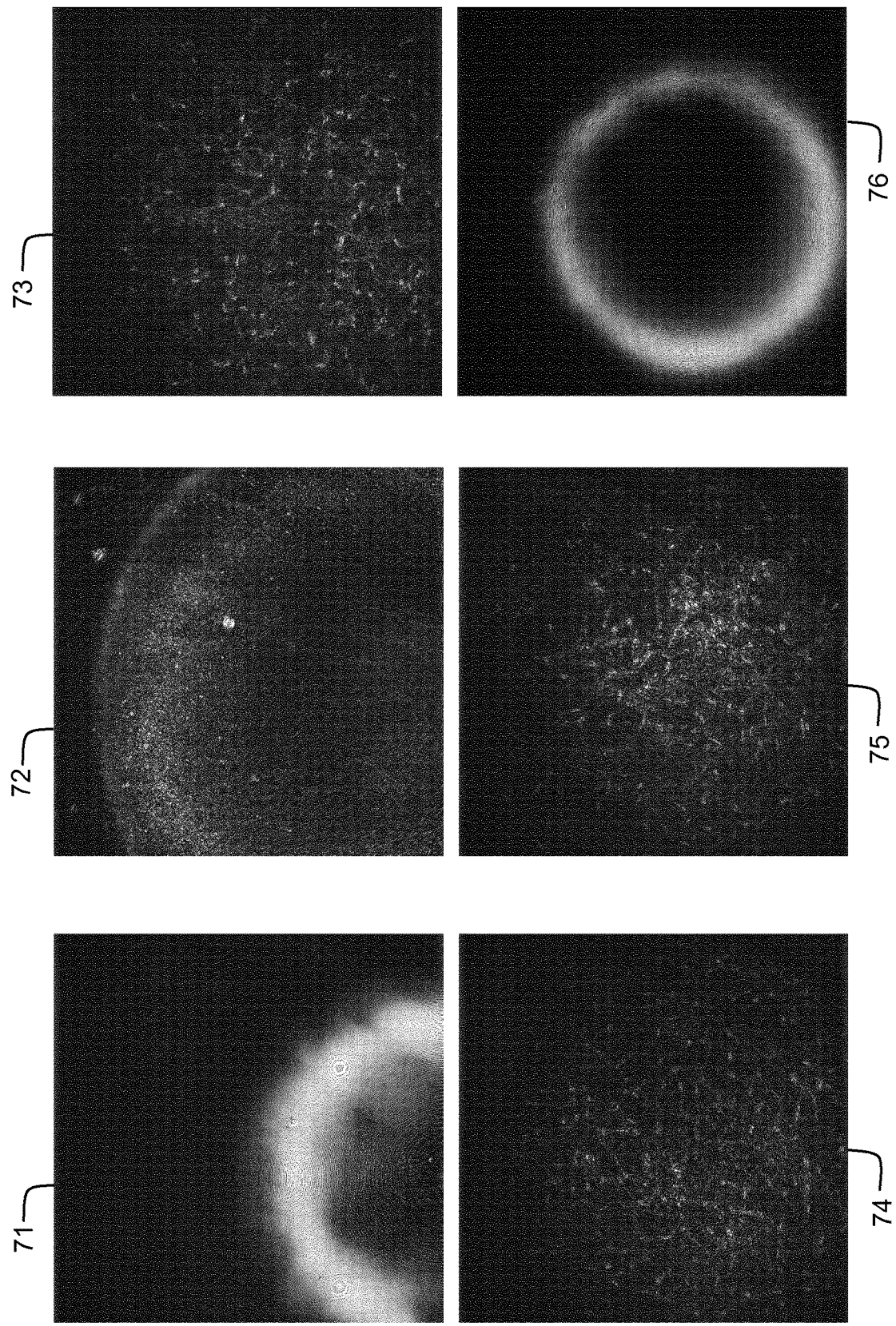
FIG. 7 shows FFOCT images of in-depth layers of the in vivo human cornea acquired using phase shifting by the natural eye movements (no move of the reference mirror).

FIG. 7 illustrates images of in-depth layers of the cornea acquired using consecutive two-dimensional interferometric signals which are phase shifted only by the natural eye movements, i.e. no move of the reference mirror is made. LED was emitting 850 nm wavelength light. The light spectrum was 30 nm wide, resulting in 7.8 μm thickness of the optical slice. Camera was set to acquire 550 direct images per second. Each image was acquired by integrating the light during the exposure time of 1.75 ms. During the exposure time the sample was moving and changing the optical phase ψ(t) of the interferometric signals. By subtracting two consecutive direct images from the camera, we subtract the two integrals over time-varying phase from the formula above and obtain the FFOCT images. The FFOCT signal depends on the function ψ(t) during the time from $T_0$ to $T_2$.

In FIG. 7, images 71 to 76 show respectively the reflection from the epithelium and tear film (71), the epithelium and sub-basal nerves (72), the anterior, middle and posterior stroma (73-75) and the endothelium (76) of in vivo human cornea.

Figure 8:
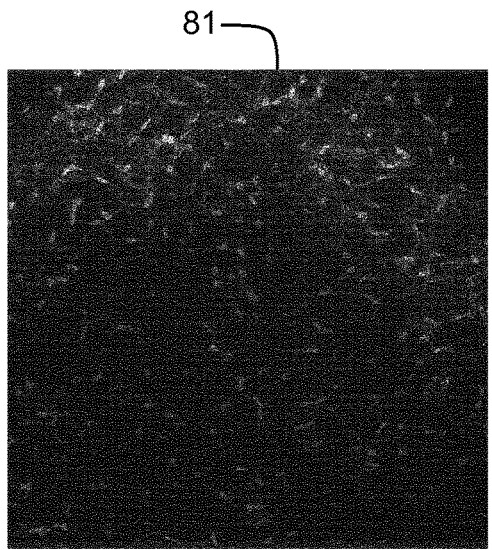
FIG. 8 shows FFOCT images of in-depth layers of the in vivo human cornea (stroma) acquired using phase shifting by the natural eye movements (no move of the reference mirror) at different camera exposure times.
Figure 8:
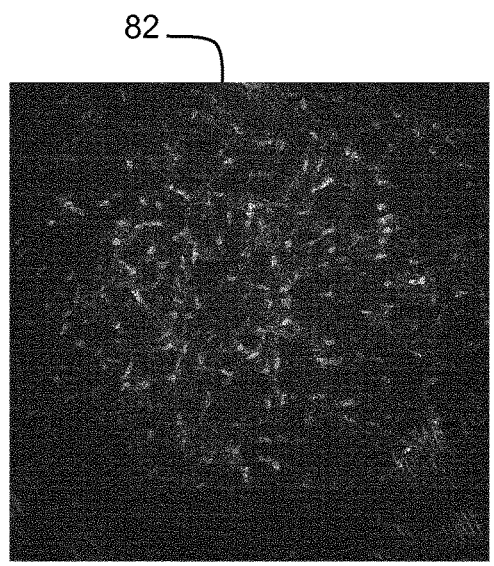
Figure 8:
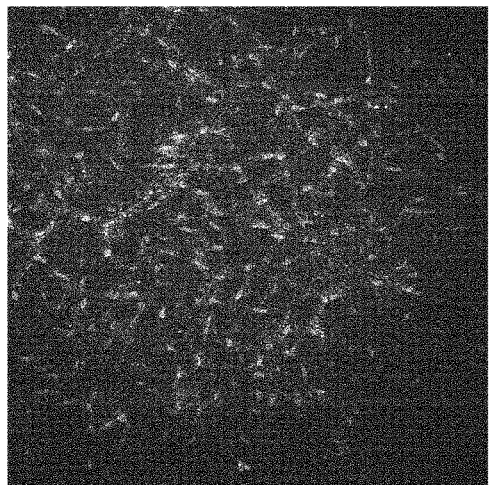
Figure 8:

FIG. 8 illustrates images 81, 82, 83, 84 of in-depth stromal layer of the cornea acquired using different camera exposure times (and, therefore, different camera frame rates of 550 frames/second, 300 frames/second, 200 frames/second and 100 frames/second, respectively). The images are captured in the same conditions than in FIG. 7, i.e. using consecutive two-dimensional interferometric signals which are phase shifted only by the natural eye movements, i.e. no move of the reference mirror is made.

The applicants have shown that such embodiment enable to retrieve very good quality images and considerably simplify the system without the need of camera-piezo synchronization.

Although described by way of a number of detailed example embodiments, the systems and methods for in vivo, full-field interference microscopy imaging of a scattering three-dimensional sample according to the present description comprise various variants, modifications and improvements that will be obvious to those skilled in the art, it being understood that these various variants, modifications and improvements fall within the scope of the invention such as defined by the following claims.

The invention claimed is:

1. A method for in vivo, full-field interference microscopy imaging of a scattering three-dimensional sample, comprising:
    disposing the sample in an object arm of an interference device of a full-field OCT imaging system, wherein said interference device further comprises a reference arm with an optical lens and a first reflection surface;
    producing, at each point of an imaging field, an interference between a reference wave obtained by reflection of incident light waves on an elementary surface of the first reflection surface corresponding to said point of the imaging field and an object wave obtained by backscattering of incident light waves by a voxel of a slice of the sample at a given depth, said voxel corresponding to said point of the imaging field,
    acquiring, using an acquisition device of said full-field OCT imaging system, a temporal succession of two-dimensional interferometric signals resulting from the interferences produced at each point of the imaging field;
    storing, for each two-dimensional interferometric signal, a time of acquisition;
    providing, at each time of acquisition of the two-dimensional interferometric signals, cross-sectional images (X-Z) of both the sample and said first reflection surface of said full-field OCT imaging system using an OCT imaging system;
    determining a plurality of en face images (X-Y) of a plurality of slices of the sample, each en face image being determined from at least two two-dimensional interferometric signals having a given phase shift;
    determining from the cross-sectional images provided by the OCT imaging system at the times of acquisition of each of said two two-dimensional interferometric signals a depth (z) for each en face image (X-Y) of said plurality of slices; and
    determining a 3D image of the sample from said plurality of en face images of said plurality of slices of the sample and depths, wherein:
        determining each en face image of the plurality of en face images comprises selecting, in said temporal succession of two-dimensional interferometric signals acquired by the acquisition device, at least two two-dimensional interferometric signals having said phase shift, wherein said phase shift is induced by in vivo movements of the sample.

2. The method according to claim 1, wherein said full-field OCT imaging system and said OCT imaging system being mounted on a moving platform, the method further comprises moving said platform at least along an optical axis (Z) of the object arm to determine said plurality of en face images (X-Y).

3. The method according to claim 2, wherein said reference arm being mounted on a moving platform, the method further comprises moving said platform to compensate for defocus.

4. The method according to claim 1, further comprising moving said platform at least along a direction (X, Y) perpendicular to said optical axis of the object arm.

5. The method according to claim 1, wherein said object arm being mounted on a moving platform, the method further comprises moving said platform along an optical axis (Z) of the object arm to determine said plurality of en face images (X-Y).

6. The method according to claim 5, wherein said reference arm being mounted on a moving platform, the method further comprises moving said platform to compensate for defocus.

7. The method according to claim 1, wherein said reference arm being mounted on a moving platform, the method further comprises moving said platform along an optical axis (X) of the reference arm to compensate for defocus, to determine said plurality of en face images (X-Y).

8. The method according to claim 1, further comprising position shifting said first reflection surface of the reference arm of the full-field OCT imaging system to provide said phase shift between said at least two two-dimensional interferometric signals.

9. A system for in vivo, full-field interference microscopy imaging of a scattering three-dimensional sample comprising:
    a full-field OCT imaging system for providing en face images of the sample, wherein said full-field OCT system comprises:
        an interference device comprising an object arm intended to receive the sample and a reference arm comprising an optical lens and a first reflection surface, wherein said object arm and said reference arm are separated by a beam splitter and wherein the interference device is adapted to produce, when the sample is disposed on the object arm of the interference device, at each point of an imaging field, an interference between a reference wave obtained by reflection of incident light waves on an elementary surface of the first reflection surface corresponding to said point of the imaging field and an object wave obtained by backscattering of incident light waves by a voxel of a slice of the sample at a given depth, said voxel corresponding to said point of the imaging field, and an acquisition device configured to acquire a temporal succession of two-dimensional interferometric signals resulting from the interferences produced at each point of the imaging field;

an OCT imaging system for providing at the same times of acquisition of said two-dimensional interferometric signals, cross-sectional images of both the sample and said first reflection surface of said full-field OCT imaging system; and a processing unit configured to:

determine a plurality of en face images (X-Y) of a plurality of slices of the sample, each en face image being determined from at least two two-dimensional interferometric signals having a given phase shift, wherein determining each en face image of the plurality of en face images further comprises selecting, using the processing unit, in said temporal succession of two-dimensional interferometric signals acquired by the acquisition device, at least two two-dimensional interferometric signals having said phase shift, wherein said phase shift is induced by in vivo movements of the sample;

determine from the cross-sectional images provided by the OCT imaging system at the times of acquisition of each of said two two-dimensional interferometric signals a depth (z) for each en face image (X-Y) of said plurality of slices; and determine a 3D image of the sample from said plurality of en face images of said plurality of slices of the sample and depths.

10. The system according to claim 9, wherein said first reflection surface of the reference arm of the full-field OCT imaging system is position shifted to provide said optical path difference between said at least two-dimensional interferometric signals.

11. The system according to claim 9, wherein said object arm of the full-field OCT imaging system further comprises an optical lens.

12. The system according to claim 9, wherein said reference arm and/or object arm of the full-field OCT imaging system can be moved with respect to said beam splitter of the interference device of said full-field OCT imaging system.

13. The system according to claim 9, further comprising a moving platform, wherein said full-field OCT imaging system and said OCT imaging system are mounted on said moving platform.

14. The system according to claim 9, wherein the OCT imaging system is a spectral domain OCT imaging system, a time-domain OCT imaging system, or a swept-source OCT imaging system.

* * * * *